(12) United States Patent
Cuscuna et al.

(10) Patent No.: US 11,452,501 B2
(45) Date of Patent: Sep. 27, 2022

(54) VARIABLE CONFIGURATION BENDING NECK FOR AN ARTICULATING ULTRASOUND PROBE

(71) Applicant: KONINKLIJKE PHILIPS N.V., Eindhoven (NL)

(72) Inventors: Dino Francesco Cuscuna, Eindhoven (NL); Kathryn Jinks, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 483 days.

(21) Appl. No.: 15/551,735

(22) PCT Filed: Mar. 2, 2016

(86) PCT No.: PCT/IB2016/051166
§ 371 (c)(1),
(2) Date: Aug. 17, 2017

(87) PCT Pub. No.: WO2016/139589
PCT Pub. Date: Sep. 9, 2016

(65) Prior Publication Data
US 2019/0117193 A1 Apr. 25, 2019

Related U.S. Application Data

(60) Provisional application No. 62/126,750, filed on Mar. 2, 2015.

(51) Int. Cl.
*A61B 8/00* (2006.01)
*A61B 1/005* (2006.01)
(Continued)

(52) U.S. Cl.
CPC .............. *A61B 8/4466* (2013.01); *A61B 1/008* (2013.01); *A61B 1/0055* (2013.01);
(Continued)

(58) Field of Classification Search
CPC ......... A61B 8/4466; A61B 8/12; A61B 8/445; A61B 1/00078; A61B 1/0055;
(Continued)

(56) References Cited

U.S. PATENT DOCUMENTS 5,105,819 A * 4/1992 Wollschlager ........... A61B 8/12
600/141
6,364,828 B1 * 4/2002 Yeung .................. A61B 1/0056
174/68.3

(Continued)

FOREIGN PATENT DOCUMENTS

JP H05111453 A 5/1993
JP 2004105289 A 4/2004
(Continued)

OTHER PUBLICATIONS

International Search Report and Written Opinion for International Application No. PCT/IB2016/050952, filed Feb. 23, 2016, 16 pages.
(Continued)

*Primary Examiner* — Amelie R Davis
*Assistant Examiner* — John Denny Li

(57) ABSTRACT

A bending neck for an articulating ultrasound probe has a variable configuration whereby different sections of the bending neck can be bent into different curvatures. In one implementation a rigid member is extended into the bending neck, setting the deflection point for a section of the bending neck at the end of the rigid member. In another implementation the links of the bending neck have different lengths, causing different sections to have different radii of maximum curvature. In another implementation the bending neck is encased in a sheath which exhibits regions of different durometer, thickness, or spacing of points of attachment to the bending neck.

20 Claims, 4 Drawing Sheets

(51) Int. Cl.
*A61B 1/00* (2006.01)
*A61B 1/008* (2006.01)
*A61M 25/01* (2006.01)
*A61B 8/12* (2006.01)
*A61B 17/00* (2006.01)

(52) U.S. Cl.
CPC ............ *A61B 1/00078* (2013.01); *A61B 8/12* (2013.01); *A61B 8/445* (2013.01); *A61M 25/0138* (2013.01); *A61B 2017/00314* (2013.01); *A61B 2017/00323* (2013.01); *A61M 25/0147* (2013.01); *A61M 2025/0161* (2013.01)

(58) Field of Classification Search
CPC .......... A61B 1/008; A61B 2017/00314; A61B 2017/00323; A61M 25/0138; A61M 25/0147; A61M 2025/0161
See application file for complete search history.

(56) References Cited

U.S. PATENT DOCUMENTS

| | | |
|---|---|---|
| 2004/0044270 A1 | 3/2004 | Barry |
| 2005/0261548 A1 | 11/2005 | Machiya et al. |
| 2005/0272978 A1 | 12/2005 | Brunnen et al. |
| 2007/0049800 A1 | 3/2007 | Boulais |
| 2007/0239022 A1* | 10/2007 | Harhen ............... A61B 1/00071 600/459 |
| 2009/0093679 A1 | 4/2009 | Suigetsu et al. |
| 2009/0234191 A1 | 9/2009 | Kitagawa et al. |
| 2010/0114270 A1 | 5/2010 | O'Connor et al. |
| 2010/0168519 A1* | 7/2010 | Matsuo ............... A61B 1/00071 600/139 |
| 2010/0261964 A1* | 10/2010 | Danitz ................. A61B 1/0053 600/141 |
| 2010/0287755 A1 | 11/2010 | Korner |
| 2010/0312056 A1 | 12/2010 | Galperin et al. |
| 2011/0230718 A1 | 9/2011 | Akui |
| 2011/0270173 A1 | 11/2011 | Gibson et al. |
| 2011/0313251 A1 | 12/2011 | Kitagawa et al. |
| 2012/0116163 A1 | 5/2012 | Lutze et al. |
| 2012/0190988 A1 | 7/2012 | Harhen |
| 2013/0060239 A1* | 3/2013 | Hinman ............... A61B 1/0055 606/1 |
| 2013/0190561 A1 | 7/2013 | Oskin et al. |
| 2014/0053940 A1 | 2/2014 | Konstorum et al. |
| 2014/0144970 A1* | 5/2014 | Aranyi ................ A61B 17/068 227/177.1 |
| 2014/0180009 A1 | 6/2014 | Tanii |
| 2014/0349485 A1 | 11/2014 | Umekawa et al. |
| 2015/0005578 A1* | 1/2015 | Jorgensen ........... A61B 17/295 600/109 |
| 2015/0320295 A1* | 11/2015 | Belson .................. A61B 34/30 600/141 |
| 2016/0151122 A1* | 6/2016 | Alvarez ........... A61B 17/00234 604/95.04 |
| 2018/0008805 A1* | 1/2018 | Pleijers .......... A61B 17/320016 |

FOREIGN PATENT DOCUMENTS

| | | |
|---|---|---|
| JP | 2007236751 A | 9/2007 |
| JP | 2008259634 A | 10/2008 |
| JP | 2011067423 A | 4/2011 |
| WO | 2008146510 A1 | 12/2008 |

OTHER PUBLICATIONS

International Search Report and Written Opinion for International Application No. PCT/IB2016/051166, filed Mar. 2, 2016, 16 pages.

\* cited by examiner

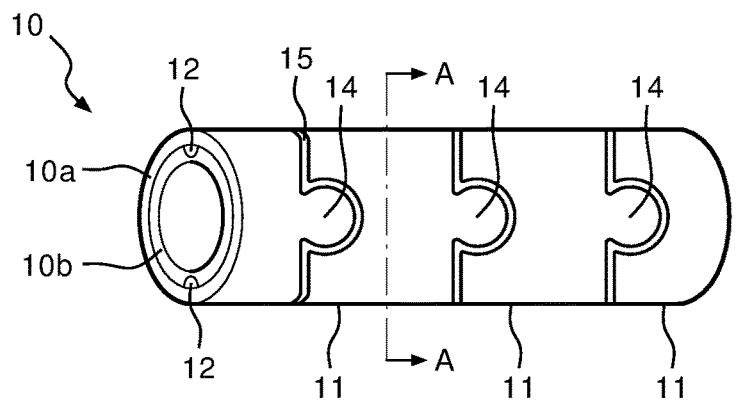
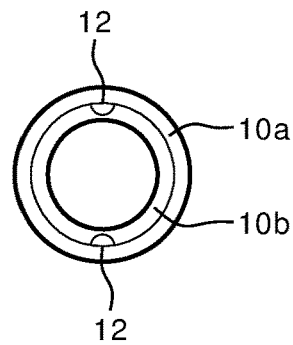
FIG. 1          FIG. 1A
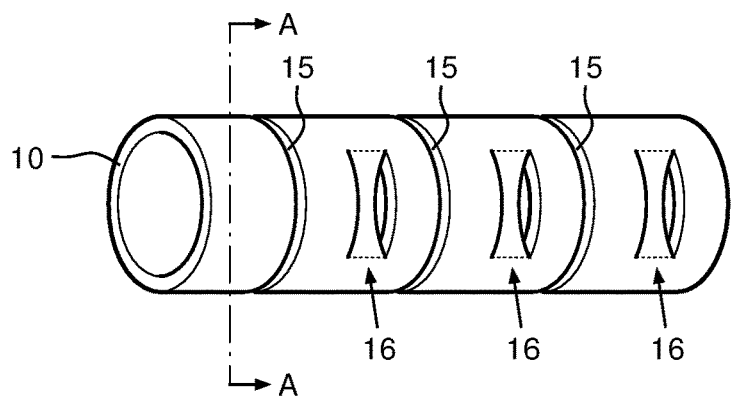
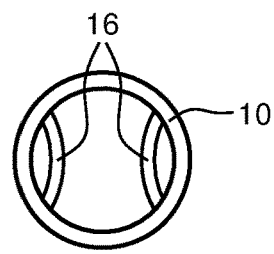
FIG. 2          FIG. 2A
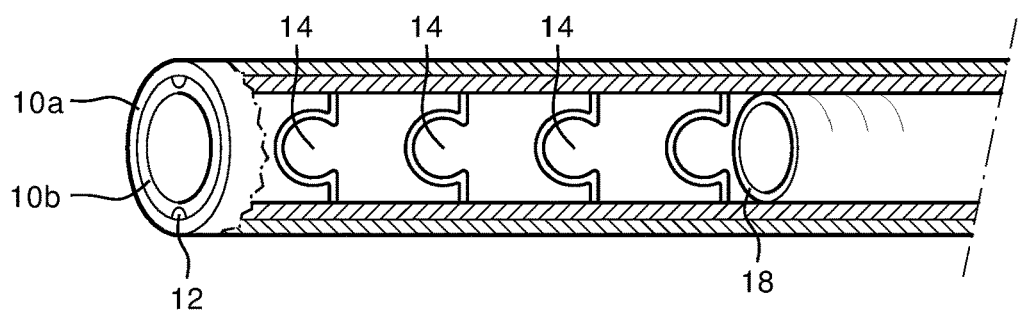
FIG. 3

VARIABLE CONFIGURATION BENDING NECK FOR AN ARTICULATING ULTRASOUND PROBE

This application is the U.S. National Phase application under 35 U.S.C. § 371 of International Application No. PCT/IB2016/051166, filed on Mar. 2, 2016, which claims the benefit of Provisional Application Ser. No. 62/126,750, filed Mar. 2, 2015. These applications are hereby incorporated by reference herein.

This invention relates to ultrasonic imaging probes and, in particular, to bending necks for articulating ultrasound probes.

Some ultrasound probes are designed for imaging from within the body, including catheter probes and transesophageal echocardiography (TEE) probes. In these probes the imaging transducer is located at the tip of the probe, which is generally designed to be articulated by the operator so as to obtain the desired view. The preferred way to articulate the probe tip, particularly in the case of TEE probes, is by means of a distal section of the catheter or gastroscope referred to as a bending neck. The bending neck is formed by a series of links which are pivotally connected to each other. This enables each link to move slightly with respect to its adjoining links and hence the entire section of links can be made to controllably articulate over a substantial angle of bending. Control of the articulation is done by cables extending through the probe and the bending neck which are wrapped about the shaft or pulley of a control knob or motor in the control unit at the proximal end of the probe. As the operator turns a knob or actuates a motor, a desired cable is pulled, which bends the articulating neck section of the probe. Generally the pivot axis between links alternates by 90° from link to link so that some axes can bend in the 0°-480° directions while the others can bend in the 90°-270° directions. The use of two controls and control cables for these two axis directions enables the operator to articulate the bending neck in any of these directions or any direction in between. The links and hence the bending neck is hollow, enabling the wiring for the transducer at the distal tip as well as other items such as guide wires and surgical tools to pass through the probe for operation at or through the tip of the probe.

The fabrication and assembly of a bending neck for an articulating probe can be painstaking and costly. Each link of the neck must be individually formed, then the links are joined by pins or rivets so that they will pivot with respect to each other. It is desirable to have an easier and less costly way to build a bending neck, yet still have the wide range of articulation and articulation control which users demand.

In accordance with the principles of the present invention, a bending neck for a controllably articulating ultrasound probe is provided which is formed from a single tube or nested tube set. The tube is etched or machined to form individual, pivoting links. A groove formed in one of the tubes of the nested tube set, or indentations in a single tube provide the control cable passageway. The bending neck curvature is formed to be variable, as by the use of movable bending points, multiple control cable anchor points, varying pivot axis spacing, and multi-durometer neck sheaths.

In the drawings:

FIGS. 1 and 1A illustrate a section of a bending neck formed from a single nested set of two tubes.

FIGS. 2 and 2A illustrate a section of a bending neck formed from a single tube, including an integral control cable passageway.

FIG. 3 illustrates a bending neck of the present invention with a variable bending deflection point.

Figure 4:
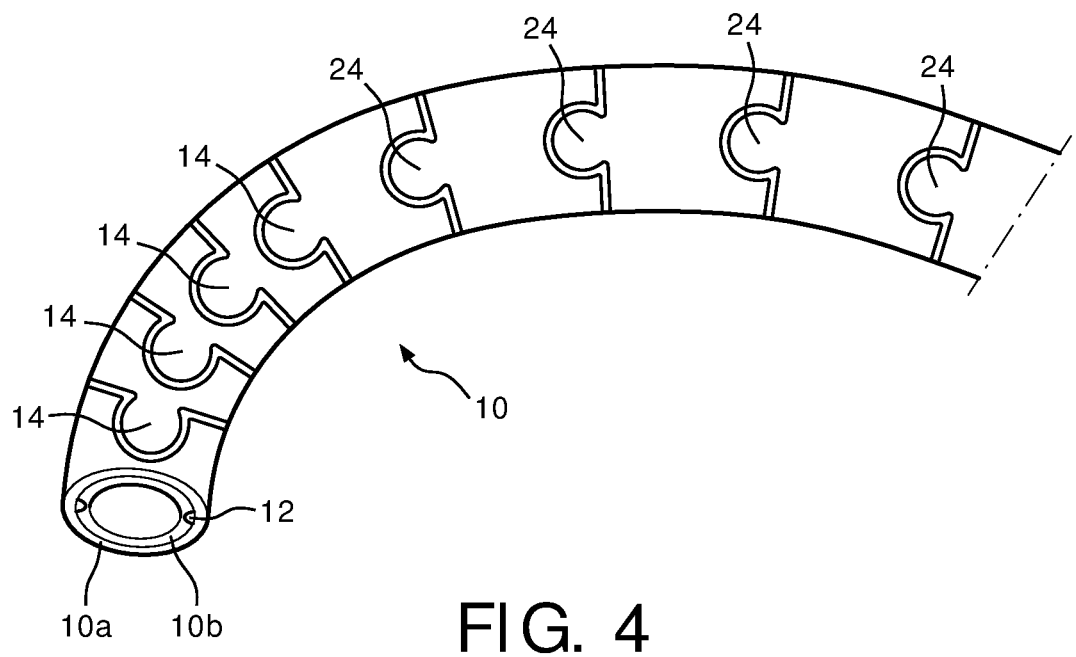
FIG. 4 illustrates a bending neck with varied link spacing to provide variable articulation.

Referring first to FIG. 1, a single piece bending neck 10 for an articulating ultrasound probe is shown which is formed of two concentric tubes, generally made of a metal such as stainless steel. The inner tube 10b fits tightly within the outer tube 10a. Before insertion, two longitudinal grooves 12 are formed on opposite sides along the length of the outside of tube 10b. These grooves form passageways for control cables that control the articulation of the bending neck as described below. The grooves 12 are clearly shown in the cross-sectional view of FIG. 1A. With the two tubes concentrically positioned, they are then cut into separate links 11 by laser cutting toward the longitudinal axis of the tube or by another machining technique. The links are formed so as to remain movably connected to each other, as by lobes 14 extending from one link to the next and located on opposite sides of the links. These lobes and the spacing between the links formed by the machining process enable the adjacent links to move and pivot with respect to each other about axes extending through opposing lobes on opposite sides of the links. While each link may only pivot a small angle with respect to its neighbor, a number of successive links forming a bending neck may together bend in a considerable curve. This is the desired articulation, significant enough to be able to position the distal end of the probe where needed, but not sharp enough at any articular point so as to bind the wires, tools, and other items passing through the central lumen of the bending neck.

FIG. 2 illustrates a second implementation of a single piece bending neck, this time using just a single tube 10. The tube 10 is machined into separate connected links as described above, the grooves 15 between separate links being shown in this drawing. Since the inner tube used for the control cable groove is not present in this single tube implementation, a series of ring-like indentations 16 are formed on opposite sides of the tube to convey the control cables through the bending neck. Two parallel cuts are made through the tube wall, then the area between the cuts is pressed inward, forming the indentations as clearly shown in the cross-sectional view of FIG. 2A. The indentations are formed on the tube sides which are 90° around the tube from the lines of pivot lobes 14, which are on the top and bottom and cannot be seen in the view of FIG. 2. As the control cables passing though the indentations on opposite sides of the tube are pulled after being anchored at the distal end of the bending neck. They will respectively cause the neck to bend into and out of the plane of the drawing of FIG. 2.

There are a number of ways that the bending of a bending neck of the present invention can be controlled and adjusted. One control technique is to control the deflection point from which the bending takes place. FIG. 3 illustrates a technique in which a rigid member 18 is located in the bending neck with its distal end at the desired deflection point. In this case the rigid member is a tube 18 and this partially cut-away view shows links to the left of the tube 18 which are free to pivot about their pivot lobes, while the links through which the tube is located are immobilized from pivoting. The position of the deflection point is adjustable by adjusting the extension of the rigid member 18 into and out of the bending neck.

The angle subtended by the curvature of a section of the bending neck can be set by selectively determining the lengths of individual links as illustrated by the bending neck 10 of FIG. 4. In this implementation the links to the left with pivot lobes 14 are relatively short and the length of these links can bend with a relatively shorter radius of curvature. The larger links to the right with the pivot lobes 24 will bend maximally with a relatively larger radius of curvature. In addition, the different size links have different moments, which determine which set of links will bend first when commonly controlled. The smaller links with the pivot lobes 14, having smaller moments, will bend first. This is useful, for instance, when the placement of a transducer at the distal tip of the smaller links (left side of the drawing) is being controlled. The articulation of both sections of the bending neck is set to approximately the desired position by pulling relatively forcefully on the control cables in the grooves 12 and thereby causing both sections to bend. With the transducer near its desired position, light pulling of the cables is used to move only the distal section of smaller links to finely adjust the final desired position of the transducer.

Figure 5:
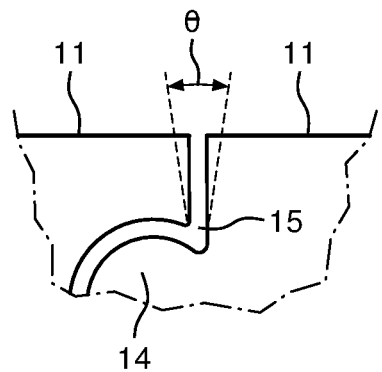
FIG. 5 is a detailed view of a technique for determining the link-to-link articulation angle for a bending neck of the present invention.

The degree of pivoting between adjacent links is a function of the groove that is machined through the tube to form separate links. FIG. 5 is a partial side view of a portion of a bending neck where separate links 11 have been formed by machining groove 15 through the tube. The two links can pivot around pivot lobe 14 by the width of the groove 15, opening and closing the groove 90° on either side of the axis of the pivot lobes. If greater pivoting is desired the groove can be machined with a tapered width with a maximum opening of theta above and below the pivot lobes. The relative pivoting of the adjacent links is thereby increased to the dimension of angle theta.

Figure 6:
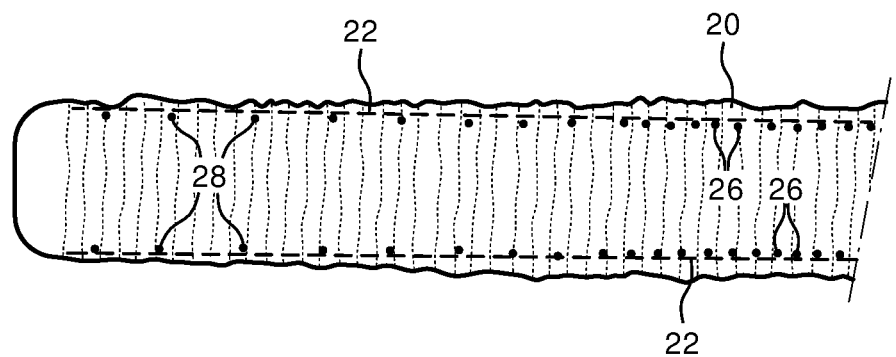
FIG. 6 illustrates a variable durometer sheath which provides variable bending for a bending neck of the present invention.

Another technique for providing variable bending of a bending neck is to enclose the bending neck in a sheath with a variable durometer. FIG. 6 illustrates a sheath 20 over a bending neck with a variable durometer from the distal end to the left to the proximal end of the bending neck. The sheath is relatively stiffer (higher durometer) to the right, which becomes less stiff toward the distal end of the sheath. When the control cables are actuated to bend the bending neck, the distal end will bend first and more easily than the higher durometer proximal section of the bending neck. The durometer can be set by the choice of materials used along the length of the sheath. Another way to achieve the same result is to vary the thickness of the sheath material along the length of the sheath. The dashed lines 22 in FIG. 6 indicate that the sheath 20 is thicker toward its proximal (right) end than it is toward and at the distal end. Yet another way to achieve the same result is through the way in which the sheath is affixed to the bending neck. In the example of FIG. 6 the sheath 20 is tacked to the bending neck at closely spaced points 26 along the proximal portion of the bending neck, and is tacked to the bending neck at more widely spaced points 28 along the distal portion of the bending neck. This will cause the distal portion of the bending neck to bend more easily and readily than the proximal portion.

Figure 7:
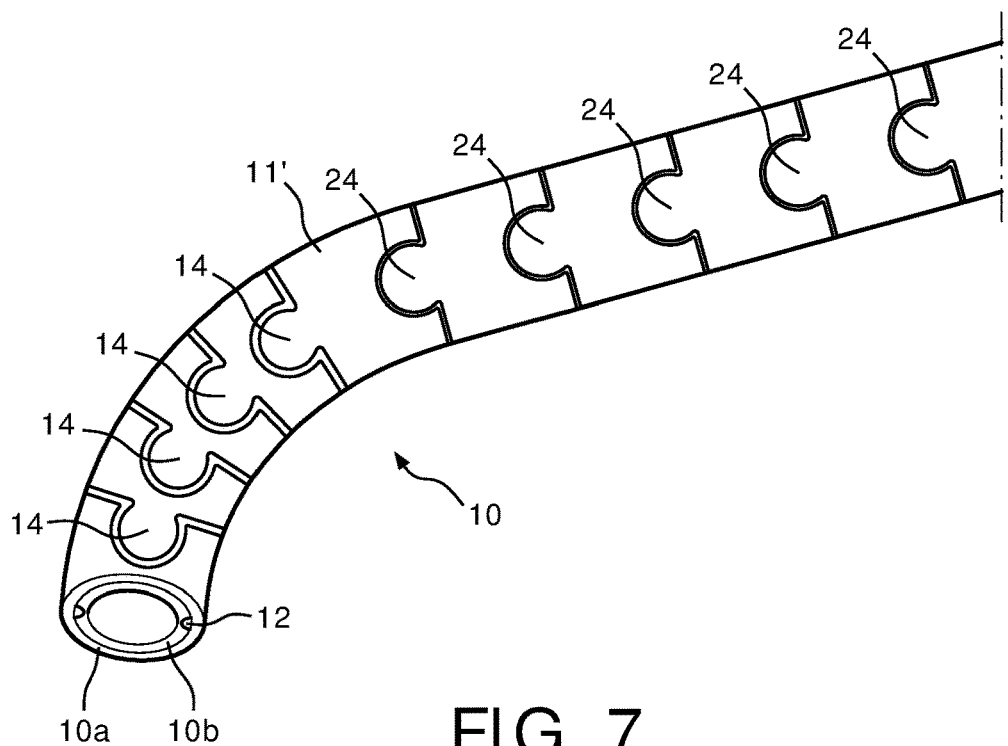
FIGS. 7 and 8 illustrate the use of multiple control cable anchor points to controllably vary the bending of a bending neck of the present invention.
Figure 8:
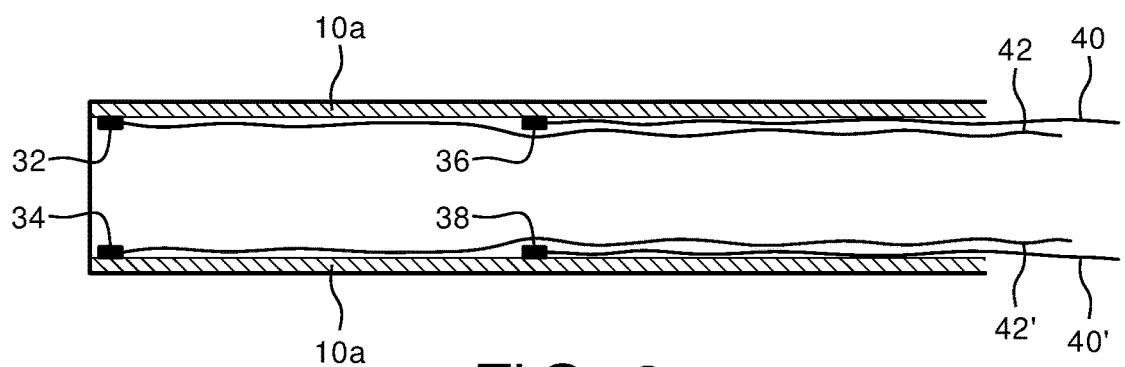

In some implementations it may be desirable to controllably bend a section of a bending neck at some times, and lock it in an unbent configuration at others. FIG. 7 illustrates an implementation of this feature using the embodiment of FIG. 4. In this case there are two sets of control cables, 40-42' and 42-42', extending through the control cable passageways 12. The ends of cables 40-40' are anchored by attachment to the distal link (leftmost) of the bending neck 10 as shown by anchor points 32 and 34 in FIG. 8. In FIG. 8 the inner tube 10b has been removed for clarity of illustration. The ends of the other set 42-42' of cables are anchored to link 11', the first link following those with pivot lobes 24, as shown by anchor points 36 and 38. When each pair of cables is pulled and relaxed in complementary fashion, the corresponding section of the bending neck is bent in the plane of the drawing, cable set 40-40' controlling the distal (small link) section and cable set 42-42' controlling the proximal (larger link) section. But when both of cables 42-42' are pulled in unison, the links of the proximal section are pulled together and locked into a straight configuration as shown in FIG. 7. The distal section of the bending neck can still be controllably articulated by use of cables 40-40'. When cables 40 and 40' are pulled in unison, the entire bending neck is locked in a straight configuration. Thus, by using multiple control cables and selected anchor points, different sections of a bending neck can be locked or articulated.

Figure 9:
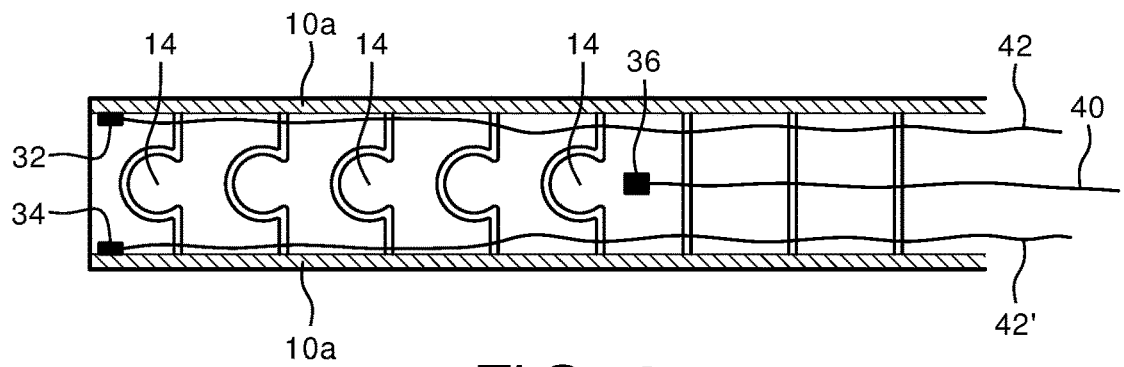
FIG. 9 illustrates a bending neck which can be controllably bent in two different planes through the use of differently anchored control cables.

In the implementation of FIG. 7 the pivot lobes are all on the front and back of the bending neck, which allows both articulating sections to be curved in the same plane, the plane of the drawing. A single set of control cable passageways 12 accommodates both sets of cables for this articulation. FIG. 9 illustrates an implementation in which pivot lobes 14 are formed in the front and back sides of the tube and hence their pivot axes are all normal to the plane of the drawing. The pivot lobes 24 of the proximal section of the bending neck, however, are formed on the top and bottom of the tube and have their pivot axes parallel to the plane of the drawing. This means that the distal section with pivot lobes 14 can be curved in the plane of the drawing whereas the proximal section of links can be curved orthogonally into and out of the drawing plane. To control these different actions different sets of control cables are used. Cables 42 and 42' extend through cable passageways 12 and are anchored at the ends at anchor points 32 and 34. These cables control the articulation of the distal (leftmost) section of the bending neck. The control cables 40 and 40' for the proximal section of the bending neck are oriented 90° around the circumference of the tube from cables 42 and 42'. These control cables must pass through their own, differently positioned control cable passageways oriented 90° relative to passageways 12. These control cables 40 and 40' are anchored at the distal end of the section of links they control as shown by cable 40 anchored at anchor point 36 in the cutaway view of FIG. 9. (Cable 40' and its anchor point are cut away in this view.) When cables 42-42' are pulled the distal section of links is articulated or locked, and when cables 40-40' are pulled the proximal section of links is controlled.

Figure 10A:
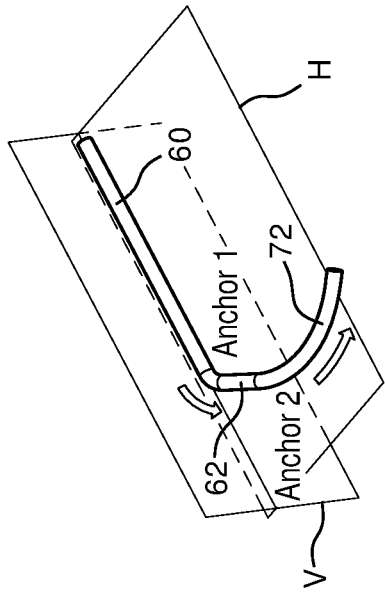
FIGS. 10a and 10b illustrate a variably articulating bending neck which is controllable articulated by two bending sections in one plane.
Figure 10B:
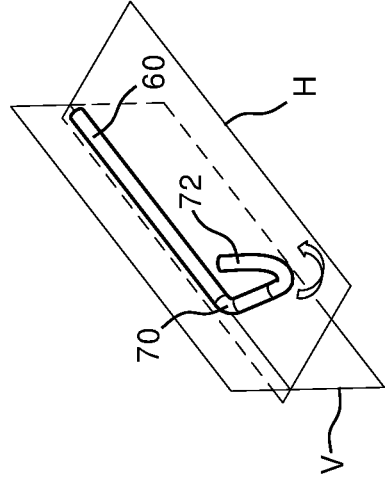

FIGS. 10a-10b are perspective views of an articulating ultrasound probe of the present invention. This probe has two straight, non-articulating sections 60 and 62 and two articulating sections 70 and 72. Like the implementation of FIG. 7, the articulating sections 70 and 72 articulate in the same plane, the horizontal plane H of the drawings. In FIG. 10a the short articulating section 70 is curved by control of its cables anchored at the distal end of section 70. In FIG. 10b the cable set anchored at the distal end of section 72 has been used to articulate section 72. Since all articulation is in the same plane, the pivot lobes of both sections are on the same sides of the section, and only a single pair of cable passageways is necessary for the control cables of both sections.

Figure 11A:
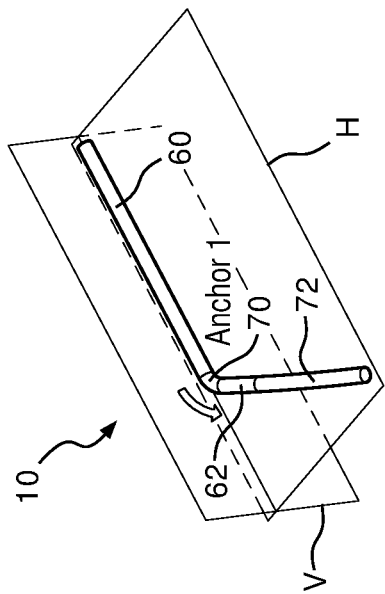
FIGS. 11a and 11b illustrate a variably articulating bending neck which is controllable articulated by two bending sections in two planes.
Figure 11B:
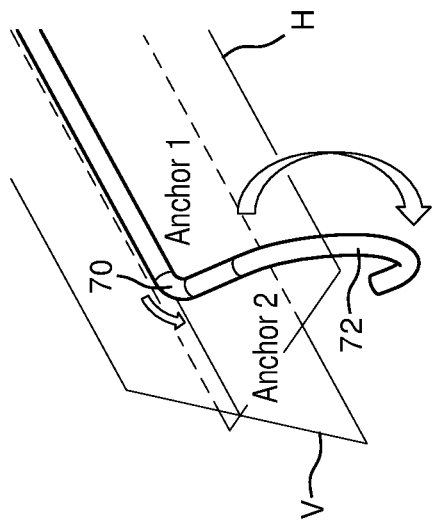

FIGS. 11a-11b are perspective views of another articulating ultrasound probe of the present invention, this one implementing articulation in two planes as in the case of FIG. 9. Like FIG. 9, the articulating section 72 of FIG. 11a has its pivot lobes, pivot axes, and control cable passageways oriented 90° around the circumference of the tube as compared with those of articulating section 70. As FIGS. 11a and 11b illustrate, the distal section 72 can be controllably articulated up and down in the vertical (V) direction.

Other variations of the above concepts will readily occur to those skilled in the art. The pivot lobes may be formed in other shapes and sizes, and pivoting between links can be provided by other, more complicated pin or rivet configurations. However, the implementations illustrated herein have the advantage of being wholly formed from a single or concentric pair of tubes. Instead of sections of identically oriented links, an articulating section can be interspersed with links pivoting at 90° with respect to each other, giving an articulating section the ability to be curved in almost any direction.

What is claimed is:

1. An articulating bending neck for an ultrasound probe comprising:
    a plurality of pivotally connected links comprising a link and an adjoining link,
    wherein each of the plurality of pivotally connected links comprises an outer tubular segment and an inner tubular segment fitting within and in contact with the outer tubular segment around an outer perimeter of the inner tubular segment,
    wherein the link and the adjoining link are completely separated by a groove and remain connected to one another by a pivot lobe of the link and a shape of the adjoining link receiving the pivot lobe,
    wherein, in an articulation configuration:
        a width of the groove is positioned between an entire end of the link and an entire opposite end of the adjoining link; and
        the link and the adjoining link are configured to pivot relative to one another around the pivot lobe by the width of the groove,
    wherein, in a locked configuration:
        the link and the adjoining link are pulled together; and
        the entire end of the link is immediately adjacent to the entire opposite end of the adjoining link such that the link and the adjoining link are prevented from pivoting relative to another,
    wherein the pivot lobe comprises an outer pivot lobe portion from the outer tubular segment and an inner pivot lobe portion from the inner tubular segment,
    wherein the groove extends through the outer tubular segment and the inner tubular segment such that:
        the groove defines the pivot lobe and the shape of the adjoining link receiving the pivot lobe; and
        the outer pivot lobe portion and the inner pivot lobe portion are aligned with one another, and
    wherein, in the articulation configuration, the link and the adjoining link are configured to pivot relative to one another without a pin or rivet joining the link and the adjoining link.

2. The articulating bending neck of claim 1, further comprising:
    a rigid member extending into a section of the articulating bending neck,
    wherein a deflection point for curvature of the section of the articulating bending neck is determined by a position of the rigid member.

3. The articulating bending neck of claim 2,
    wherein the rigid member further comprises a tube extending into the section of the articulating bending neck,
    wherein the section of the articulating bending neck comprises a subset of the plurality of pivotally connected links that are rendered inarticulable to form a straight section.

4. The articulating bending neck of claim 1, further comprising:
    a plurality of pivot axes extending through the plurality of pivotally connected links and about which the plurality of pivotally connected links pivot,
    wherein a first section of the articulating bending neck has relatively closely spaced pivot axes and a second section of the articulating bending neck has relatively more widely spaced pivot axes.

5. The articulating bending neck of claim 4, wherein the first section has a relatively smaller radius of maximum curvature and the second section has a relatively larger radius of maximum curvature.

6. The articulating bending neck of claim 4,
    wherein the first section comprises a first subset of the plurality of pivotally connected links and the second section comprises a second subset of the plurality of pivotally connected links,
    wherein the first subset of the plurality of pivotally connected links exhibit a smaller moment than the second subset of the plurality of pivotally connected links.

7. The articulating bending neck of claim 4,
    wherein the link and the adjoining link remain connected to one another by a further pivot lobe of the link and a further shape of the adjoining link receiving the further pivot lobe,
    wherein the pivot lobe and the further pivot lobe are opposite to one another around a circumference of the articulating bending neck such that the pivot axis extends through the pivot lobe and the further pivot lobe, and
    wherein the shape of the adjoining link and the further shape of the adjoining link are opposite to one another around the circumference of the articulating bending neck.

8. The articulating bending neck of claim 7, wherein the pivot lobe of the link and the shape of the adjoining link are machined portions.

9. The articulating bending neck of claim 1, further comprising:
    a sheath enclosing the plurality of pivotally connected links, wherein the sheath exhibits regions of different durometers along a length of the sheath.

10. The articulating bending neck of claim 9, wherein the regions of different durometers further comprises regions of different sheath thickness.

11. The articulating bending neck of claim 1, further comprising:
a sheath enclosing the plurality of pivotally connected links,
wherein the sheath exhibits points of attachment to the plurality of pivotally connected links along a length of the sheath,
wherein the points of attachment are more closely spaced along one section of the sheath relative to another section of the sheath.

12. The articulating neck of claim 1, further comprising:
a first control cable extending through the plurality of pivotally connected links and anchored to a distal end of a first section of the plurality of pivotally connected links at a first anchoring location, wherein, when the first control cable is pulled, the first section of the plurality of pivotally connected links is configured to articulate; and
a second control cable extending through the plurality of pivotally connected links and anchored to the distal end of the first section of the plurality of pivotally connected links at a second anchoring location,
wherein the first anchoring location and the second anchoring location are opposite to one another around a circumference of the articulating bending neck,
wherein, when the first control cable and the second control cable are pulled, the first section of the plurality of pivotally connected links are in the locked configuration to form a straight section.

13. The articulating bending neck of claim 12, further comprising:
a third control cable extending through the plurality of pivotally connected links and anchored to a distal end of a second section of the plurality of pivotally connected links at a third anchoring location; and
a fourth control cable extending through the plurality of pivotally connected links and anchored to the distal end of the second section of the plurality of pivotally connected links at a fourth anchoring location,
wherein the third anchoring location and the fourth anchoring location are opposite to one another around the circumference of the articulating bending neck,
wherein articulation of the first section of the plurality of pivotally connected links and the second section of the plurality of pivotally connected links are separately controlled.

14. The articulating bending neck of claim 13,
wherein the plurality of pivotally connected links comprises a plurality of pivot lobes, wherein the pivot lobe of the link is one of the plurality of pivot lobes of the plurality of pivotally connected links,
wherein the first section of the plurality of pivotally connected links comprises a first subset of the plurality of pivot lobes and the second section of the plurality of pivotally connected links comprises a second subset of the plurality of pivot lobes,
wherein the first subset of the plurality of pivot lobes and the second subset of the plurality of pivot lobes are aligned.

15. The articulating bending neck of claim 13,
wherein the plurality of pivotally connected links comprises a plurality of pivot lobes, wherein the pivot lobe of the link is one of the plurality of pivot lobes of the plurality of pivotally connected links,
wherein the first section of the plurality of pivotally connected links comprises a first subset of the plurality of pivot lobes and the second section of the plurality of pivotally connected links comprises a second subset of the plurality of pivot lobes,
wherein the first subset of the plurality of pivot lobes and the second subset of the plurality of pivot lobes are offset by 90° around the circumference of the articulating bending neck.

16. The articulating bending neck of claim 15, wherein the first anchoring location and the second anchoring location are offset by 90° around the circumference of the articulating bending neck from the third anchoring location and the fourth anchoring location.

17. The articulating bending neck of claim 1, wherein the plurality of pivotally connected links are sized and shaped for insertion into an esophagus for trans-esophageal echocardiography.

18. The articulating bending neck of claim 1, wherein the link and the adjoining link comprise:
a linear edge such that the groove corresponds to a first articulation angle between the link and the adjoining link; or
a tapered edge such that the groove corresponds to a second articulation angle between the link and the adjoining link, wherein the second articulation angle is greater than the first articulation angle.

19. The articulating bending neck of claim 1, wherein each of the inner tubular segment and the outer tubular segment comprise a metal.

20. The articulating bending neck of claim 1, wherein, in the articulation configuration, the plurality of pivotally connected links comprises different radii of curvature along the articulating bending neck.

* * * * *